United States Patent [19]

Tencza

[11] 4,294,819

[45] Oct. 13, 1981

[54] ALKALINE ANALGESIC CAPSULE

[75] Inventor: Thomas M. Tencza, Wallington, N.J.

[73] Assignee: Bristol-Myers Company, New York, N.Y.

[21] Appl. No.: 179,191

[22] Filed: Aug. 18, 1980

[51] Int. Cl.³ .................. A61K 9/48; A61K 31/60; A61K 33/10; A61K 33/12
[52] U.S. Cl. .................. 424/14; 424/16; 424/21; 424/37; 424/154; 424/155; 424/156; 424/157; 424/230
[58] Field of Search .......... 424/14, 16, 21, 37, 424/154, 155, 156, 157, 230

[56] References Cited

U.S. PATENT DOCUMENTS

| | | | |
|---|---|---|---|
| 2,224,256 | 12/1940 | Doushkiss | 424/230 |
| 2,447,396 | 8/1948 | Coplans | 424/230 |
| 2,698,332 | 12/1954 | Beckman | 424/230 |
| 2,801,951 | 8/1957 | Cooper | 424/230 |
| 2,888,382 | 5/1959 | Pleyte et al. | 24/230 |
| 2,889,248 | 6/1959 | Paterson | 424/230 |
| 2,918,485 | 12/1959 | Schenck et al. | 424/230 |
| 2,990,328 | 6/1961 | Lincoln | 424/230 |
| 3,019,169 | 1/1962 | Klumpp et al. | 424/230 |
| 3,323,992 | 6/1967 | Schenck | 424/230 |
| 4,167,558 | 9/1979 | Sheth et al. | 424/230 |

FOREIGN PATENT DOCUMENTS

| | | | |
|---|---|---|---|
| 808949 | 2/1937 | France | 424/21 |
| 1204580 | 9/1970 | United Kingdom | 425/37 |

OTHER PUBLICATIONS

Husa et al., III–IV Chem. Abstr. 34 #3444³⁻⁷ (1940) of J.A.Ph.A. 29: 78-86 136-141 (1940).
Husa et al., Chem. Abstr. 36 #5321 ³ (1942) of J.A.Ph.A. 31: 213-216 (1942).

*Primary Examiner*—Shep K. Rose
*Attorney, Agent, or Firm*—Irving Holtzman; George A. Mentis

[57] ABSTRACT

There is disclosed a capsule containing aspirin and alternatively other active analgesic materials in combination with an alkaline material. The composition is made stable by providing the alkaline material in a tablet form.

13 Claims, No Drawings

ALKALINE ANALGESIC CAPSULE

BACKGROUND OF THE INVENTION

This invention relates to a capsule product containing a combination of aspirin as the significant active analgesic ingredient and an alkaline material. For a long time, it has been appreciated that the coadministration of aspirin along with an alkaline material has certain distinct advantages. One of these is that the presence of the alkaline material serves to increase the rate at which the aspirin is absorbed into the bloodstream. A second benefit is that the alkaline material tends to decrease any irritation to the gastrointestinal mucosa that aspirin may cause in some subjects.

Although these are recognized benefits for the coadministration of aspirin and alkaline materials, the incorporation of these materials in a single dosage form has presented problems. Aspirin is hydrolyzed to salicylic acid by alkaline material when moisture is present with the result that some of its effectiveness as an analgesic is reduced. In the case of tabletted products, efforts have been made to stabilize these products by forming the tablets in two layers, one layer containing the aspirin and the other layer containing the alkaline material. This has proven to be relatively successful in providing a stable tablet i.e. one in which the aspirin is not readily hydrolyzed.

In the case of people who have difficulty swallowing tablets, it is also desirable to be able to administer aspirin-containing products in the form of a capsule which is generally considered to be easier to swallow than tablets. This is particularly the case when the dosage of aspirin in each dosage form is relatively large. Moreover, aspirin-containing tablets sometimes dissolve in the mouth leaving a taste that most people find objectionable. This is generally avoided when aspirin-containing products are administered in a capsule.

Efforts have been made to prepare aspirin-containing products commingled with alkaline materials in a capsule to obtain the benefits from this mode of administration. However, when the aspirin and alkaline materials were mixed together in the form of granules or powders and this mix was used to load the capsules, the resulting products did not have the requisite stability due to the presence of moisture and the intimate contact between the aspirin and the alkaline material.

BRIEF DESCRIPTION OF THE INVENTION

This invention provides a dosage form of an aspirin product containing alkaline materials which have the requisite stability and speed of reaction with stomach acid. The dosage form is a capsule either hard or soft shelled, containing the alkaline material which has previously been formed into a small tablet then loaded into the capsule and a granular or powdered mix containing the desired dosage of aspirin. The capsules are produced by filling them first with the tabletted alkaline material, then adding the aspirin composition. In this fashion, the alkaline material is effectively maintained essentially separate from the aspirin-containing material insuring minimal contact between the two. The contact which takes place is only at the surface of the small tablet of alkaline material. This greatly minimizes the changes of any significant hydrolysis of the aspirin by the alkaline material.

It is accordingly an object of the present invention to provide a capsule containing aspirin and an alkaline material which is stable i.e. the hydrolysis of aspirin by the alkaline material is greatly minimized.

Other and more detailed objects of this invention will be apparent from the following description and claims.

DETAILED DESCRIPTION OF THE INVENTION

The present invention provides capsules containing analgesic compositions in which the active analgesic ingredient is normally unstable. More particularly, this invention provides capsules containing aspirin as the sole active analgesic ingredient. In addition, this invention provides capsules containing analgesic compositions with other active analgesics in addition to aspirin and compositions containing other pharmaceutically active ingredients with or without non-aspirin analgesics. Thus, this invention provides stable analgesic dosages which are in the form of capsules containing an analgesic composition comprising a significant amount of aspirin and an alkaline material.

The small alkaline tablet which forms part of the analgesic composition of the present invention may comprise a single or combination of alkaline materials. In addition, it may also contain other ingredients which are compatible with the alkaline material in the tablet.

As used herein, the term "aspirin mixture" refers to that powder and/or granular portion of the composition that contains the aspirin but may also contain other compatible powder or granular materials. The term "alkaline tablet" refers to the small tablet which contains the alkaline material but may also contain other compatible ingredients. Unless otherwise specified, percent is given as percent by weight based on the total weight of the product contained in the capsule shell.

Aspirin Mixture

The principal ingredient on a weight basis in the aspirin mixture will usually be aspirin. This will ordinarily take the form of a powder or dry granulation that may vary widely in particle size. In the typical cases, this will usually fall within the range of from about 100% which pass through a 12 mesh screen to about 100% which pass through a 80 mesh screen.

The quantity of aspirin that will be contained in each capsule will vary depending on the dosage regimen. If the regimen requires, for example, four capsules at a time, the quantity of aspirin that will be contained in each capsule may be as low as 81 mg. Ordinarily, the recommended regimen will call for two capsules at a time in which event the capsules will contain a minimum of 325 mg. of aspirin. However, it should be understood that the regimen depends upon the condition of the patient in the judgment of the physician.

The invention also provides extra-strength aspirin capsules in which each capsule contains at least 400 mg. of aspirin. If this quantity of aspirin is contained in a tablet together with an alkaline material, the tablet would be a very large tablet and especially difficult to swallow. However, the same quantity of material contained in a capsule in accordance with the present invention results in a dosage form that is much more readily swallowed.

The amount of aspirin which can be contained in the capsule is not critical to this invention, and the upper limit is limited only by the feasibility of swallowing the size of the capsule that is required to contain this material. As a practical matter, this will rarely exceed about 500 mg. of aspirin per capsule. Nevertheless, a capsule ordinarily will not contain more than the recommended daily dose of aspirin.

Therefore, according to a preferred embodiment of the present invention, each capsule contains aspirin at a level within the range of from about 160 mg. to about 500 mg. per capsule. A most efficacious embodiment of this invention is a capsule containing from about 400 mg. to about 500 mg. of aspirin.

In cases in which the aspirin component contains other pharmaceutically active ingredients and particularly other analgesics, the amount of aspirin contained in each capsule may be less than the amounts discussed above. However, as stated above, the invention is not in the amount of aspirin but in the stable dosage form.

The aspirin mixture may also contain conventional excipients which are compatible with aspirin and which are well known to those skilled in the pharmaceutical arts such as, for example, starch, modified starch (e.g. product sold under the trade name "Sta-Rx"), microcrystalline cellulose (Avicel), sodium carboxymethyl starch (Explotab, Primojel).

The quantity of excipient in each capsule can vary depending upon the quantity of aspirin contained therein and the size of the capsule. Typically, the quantity of excipient in each capsule is within the range of from about 5% to about 25% by weight based on the weight of the aspirin contained in the mixture.

The aspirin mixture may also contain a lubricant which serves to facilitate the flow of powder or granular materials during filling and processing. There are a number of lubricants well known to those skilled in this art that may be employed. For example, mention may be made of the Silicone Fluids (i.e. polydimethylsiloxane), fumed silicone dioxide (e.g. Cab-O-Sil M-5), light mineral oil, and polyethylene glycol (Carbowax 400).

The quantity of lubricant in the aspirin mixture is related to the quantity of aspirin present. Typically, the quantity of lubricant in each capsule is within the range of from about 0.25 to about 4.0% by weight based on the weight of the aspirin contained in the mixture.

In addition to aspirin, other pharmaceutically active ingredients may be contained in the aspirin mixture. These may be other analgesics, analgesic potentiators, antihistamines, decongestants, and antitussive agents. By way of illustration of such other pharmaceutically active ingredients, mention may be made of acetaminophen, caffeine, chlorpheniramine maleate, phenylpropanolamine HCl, dextromethorphan, codeine and surfactants such as sodium lauryl sulfate, polyvinylpyrrolidone, polyoxyethylene (20)sorbitan monooleate (Tween 80).

Alkaline Tablet

The alkaline tablet used in this invention is a small tablet dimensioned so that it can be conveniently dropped into the open end of a capsule which is of a suitable size for use in this invention e.g. #0, #1 and #2. The capsules can be either hard shell or soft shell gelatin capsules, with hard shell preferred. The alkaline tablets will usually comprise one or more alkaline materials that are formed into a granulation by a wet granulation process to provide a material that is readily compressible to form a tablet. A variety of alkaline materials which can be used for this purpose are available in the prior art. These include such materials as magnesium carbonate, calcium carbonate, sodium bicarbonate, aluminum glycinate, aluminum hydroxide, magnesium hydroxide, magnesium trisilicate and magnesium oxide or any combination of one, two, three or more of these materials.

The quantity of alkaline material as a single ingredient or as a combination of alkaline ingredients is not critical to this invention as long as they can be formed into a suitable sized tablet. Generally, the amount of alkaline material can vary within wide limits and is usually related to the amount of aspirin contained in the aspirin component. Typically, the amount of alkaline material is present in the tablet at a level of from about 30% to about 100% by weight based on the weight of aspirin contained in each capsule.

To get the full benefit of the alkaline component insofar as it has an effect on the absorption rate of the aspirin, it is important that the alkaline tablet have a fast disintegration rate. Exceptionally good disintegration rates are obtained where the alkaline material consists of a combination of magnesium carbonate and calcium carbonate. In a preferred aspect of the present invention, the alkaline material as a combination of magnesium carbonate and calcium carbonate is present in the alkaline component and contained within the capsule at a level in the range of from about 45% to about 55% by weight based on the weight of aspirin contained in the capsule. The ratio of calcium carbonate to magnesium carbonate may also vary somewhat but typically the ratio based on weight will be in the range of from 1:1 to about 3:1. The amounts and identity of alkaline material in the capsule are not critical to this invention so long as they perform the functions required when administered.

It is also advantageous to incorporate a disintegrant in the alkaline tablet of the present product to increase the rate at which it disintegrates in the stomach. A variety of materials are known in the tabletting art which will accomplish this function. These include such materials as corn starch, potato starch, wheat starch, modified starch (e.g. Sta-Rx) and sodium carboxymethyl starch (e.g. Primojel). Ordinarily, such materials are present in the alkaline tablet at a level in the range of from about 5% to about 20% by weight based on the total weight of the alkaline tablet.

Other ingredients may be added to the alkaline tablet to improve its physical or organoleptic characteristics or to facilitate the manufacture of the alkaline tablet. Thus, an organic acid e.g. citric acid may be added to improve the hardness of the alkaline tablet to improve the ease of handling. Similarly, a lubricant such as magnesium stearate, stearic acid or silicone fluid may be added to facilitate the tabletting of the alkaline granulation.

Several processes are known to those skilled in this art that may be used in preparing the products of the present invention. In one of the preferred procedures, the alkaline tablet is prepared by first mixing the alkaline ingredient or ingredients with a disintegrant e.g. corn starch until a homogeneous mix is obtained. This mix is then moistened by a hot aqueous medium (e.g. deionized water or distilled water). If desired, the organic acid e.g. citric acid may also be added to the solution.

The resulting wet mixture is then dried and the dried material is passed through an oscillator provided with appropriate mesh openings to obtain a granulated product. Other excipients such as lubricants are added and this granulation is then pressed into a tablet.

The alkaline tablet is dimensioned so that it will contain a maximum amount of weight of material in a minimum volume so it can be readily dropped into a gelatin capsule e.g. #0 gelatin capsule. This is accomplished by forming the alkaline tablet as a spheroid or nearspheroid having a diagonal dimension of no greater than the diameter of the open end of the capsule. Usually, the diameter of the tablet at its greatest dimension will be in the range of from about 0.225" to about 0.240".

Because of the difficulty in compressing a granulation into a true spheroidal tablet in the preferred practice of this invention, a modified deep ball punch is employed. This gives a modified spheroidal tablet having the form of a solid cylinder provided with an upper and lower dome. In this case, the important dimension is the diameter of the tablet in longitudinal cross section that extends from the top of one vertical side to the bottom of the other vertical. A suitable diameter is in the range of from about 0.210" to about 0.225".

After the alkaline tablets are formed, they are fed to a filling station where each is inserted into the body of a capsule and the capsule containing the alkaline tablet is passed on to a second station where it receives the powdered aspirin mixture. After receiving the powdered aspirin mixture, the capsule is capped with the upper half of the capsule and the product is completed.

The capsules that are employed in the present invention may be conventional gelatin capsules that are well known to those skilled in this art. These may vary somewhat in size but usually they will be #0, #1, #2 and #3. Since a fast rate of absorption of aspirin into the bloodstream is a desirable feature, it is advantageous to employ a capsule which in itself is fast dissolving. With this in mind, it is useful to include in the gelatin material that constitutes the capsule about 10% by weight of calcium carbonate based on the total weight of the capsule mentioned.

The following Examples are given to further illustrate this invention. It is to be understood, however, that the invention is not limited thereto.

EXAMPLE 1

Formula CL 1561-61

| Dosage Unit Amt. mg/capsule | Item No. | Ingredients | Quantities for 60,000 capsules in grams |
|---|---|---|---|
| | | Part I Alkaline Tablet | |
| 50.00 | 1 | carbonate | 3000 |
| 120.00 | 2 | Calcium carbonate | 7200 |
| 2.50 | 3 | Citric acid (Anhy.) | 150 |
| 18.00 | 4 | Corn starch | 1080 |
| | 5 | Deionized water or Distilled water | 6000 ml. |
| 190.50 | | | |
| .38 | 6 | Magnesium stearate | 22.8 |
| 190.88 mg | | | 11452.8 |
| | | Part II Aspirin Mixture | |
| 400.00 | 7 | Aspirin 80 mesh | 24.000 |
| 66.00 | 8 | Sta-Rx 1500[1] | 3.960 |
| 2.00 | 9 | Cab-O-Sil[2] | 160 |
| | | | 28.080 gm |
| 468.00 | | wt. of aspirin mix | |
| 190.88 | | wt. of alkaline tablet | |
| 658.88 | | total weight of capsule (net) | |

Note [1]Sta-Rx 1500 - modified starch
Note [2]Cab-O-Sil - colloidal silicone dioxide M-5

Procedure
Part I-Alkaline tablet (a) Ingredients 1, 2 and 4 i.e. the magnesium carbonate, calcium carbonate and corn starch are mixed together for five minutes.
(b) Ingredient 3, i.e. the citric acid is dissolved in the total quantity of water maintained at 100° C.
(c) The solution from step (b) is introduced into the mixture from step (a) in a mixer and this combination is mixed for 10 minutes.
(d) The product resulting from step (c) is then passed through a Tornado Mill.
(e) The product coming from step (d) is dried in a fluid bed dryer to a maximum moisture content of 0.5%; the inlet temperature in dryer is at 80° C. to 90° C.; whereas, the outlet temperature is at 40° C. to 50° C.
(f) The product from step (e) is then passed through a 10 mesh oscillator and the material is collected. The magnesium stearate is added to serve as a lubricant and the resulting material is compressed into a semi-spheroidal tablet.

To prepare the semi-spheroidal tablet from the material obtained from step (f) a 7/32" modified deep ball punch is employed. This gives an alkaline tablet that weights 190.88 mg. The thickness of the tablet is within the range of from about 0.215" to about 0.220".

Part II—Aspirin Mixture (a) Ingredients 7, 8 and 9 i.e. the aspirin, Sta-Rx 1500 and the Cab-O-Sil were blended together for 15 minutes in a V-blender. Before it was employed, the Sta-Rx 1500 was dried in an oven for 2 hours at 125°–150° F. to stabilize the moisture content to a maximum of 5%. The mixture obtained from this step was used to fill the capsules.

In preparing the capsule, a #0 gelatin capsule is employed. An alkaline tablet prepared in accordance with procedure of Part I was dropped into the lower half (body) of the capsule. A plunger may be employed to insure that the tablet is pressed down toward the bottom of the capsule. About 468 mg. of the aspirin mixture is then charged into the capsule and the upper half (cap) of the capsule is applied.

EXAMPLE 2

Following a procedure similar to that described in Example 1, the following capsule was prepared:

| | CL 1565-25 | |
|---|---|---|
| Alkaline Tablet | mg/tablet | gm per batch (30,000) |
| Magnesium carbonate | 50 | 1500 |
| Calcium carbonate | 100 | 3000 |
| Starch, corn | 18 | 540 |
| Citric acid | 2.5 | 75 |
| | 170.5 mg | 5115 gm |

Three thousand ml of water at 100° C. was used to dissolve the citric acid and to prepare the batch of material for granulation and tabletting. The moisture content of the alkaline material was 0.5% maximum.

This granulation was used to prepare two sets of alkaline tablets weighing about 170.5 mg but prepared using different size punches i.e. ¼" S.C. (standard concave) and 7/32" S.C. punches respectively, each tablet having a 20 sec. disintegration time. The tablets so obtained were employed in preparing the following capsules:

| (A) Formula CL 1565-25A | |
|---|---|
| Aspirin 40 mesh | 325 mg |
| Sta-Rx 1500 | 100 |
| Alkaline tablets 7/32" S.C. | 170.5 |
| | 595.5 mg |

Filled by hand into Capsule #0 (white)

| (B) Formula CL 1565-25B | |
|---|---|
| Aspirin 40 mesh | 325 mg |
| Sta-Rx 1500 | 100 |
| Alkaline tablets ¼" S.C. | 170.5 |
| | 595.5 mg |

Filled by hand into Capsule #0 (white)

EXAMPLE 3

Alkaline Granulation (CL 1565-42)

Using a procedure similar to that described above for the preparation of the alkaline granulation, the following granulation was prepared:

| Alkaline Granulation | mg/tablet | batch wt. kg. |
|---|---|---|
| Magnesium carbonate | 50 | 10.000 |
| Calcium carbonate | 100 | 20.000 |
| Citric acid | 2.5 | .500 |
| Starch | 18 | 3.600 |
| Water QS 100° C. | | |
| | 170.5 | 34.100 kg |

40 liters of water were employed in the preparation of the granulation. This granulation had a moisture content after drying falling within the range of from 0.1 to 0.2%.

The alkaline tablets were prepared by blending the above granulation with silicone fluid 360 and magnesium stearate in accordance with the following formula:

| CL 1565-44 | |
|---|---|
| | wt/grams |
| Alkaline granulation CL 1565-42 | 1705.0 |
| Silicone Fluid 360 | 8.525 |
| Magnesium stearate | 1.705 |
| | 1715.230 gm |

This material was compressed into tablets using a 7/32" special spheroid punch. Each tablet weighed about 171.5 mg. and had a thickness within the range of 0.205" to 0.210".

These tablets were used to prepare two groups of capsule products identified by the codes CL 1565-44A and CL 1565-44B. One tablet was placed in each gelatin capsule #0 followed by the addition of the aspirin mix. The formulas for the respective products are as follows:

| CL 1565-44A | |
|---|---|
| | wt/gm |
| Alkaline tablet CL 1565-44 | 0.1715 |
| Aspirin 40 mesh | 0.3250 |
| Sta-Rx 1500 | 0.2195 |
| Silicone Fluid 360 | 0.0050 |
| | 0.7210 gm |

| CL 1565-44B | |
|---|---|
| | wt/gm |
| Alkaline tablet CL 1565-44 | 0.1715 |
| Aspirin 10% starch granulation | 0.3611 |
| Sta-Rx 1500 | 0.1834 |
| Silicone Fluid 360 | 0.0050 |
| | 0.7210 gm |

To demonstrate the stability of the present composition containing an alkaline tablet and an aspirin mixture in a capsule as compared with the same composition excepting for the fact that the alkaline material was present in the capsule as a granulation and not a tablet, the following test was carried out:

Samples of capsules, CL 1565-44A, CL 1565-44B described above and CL 1565-44D were torture tested at 60° C./60% RH for approximately 88 hours.

Samples CL 1565-44A and B contain an alkaline tablet which consists of 50 mg $MgCO_3$ and 100 mg $CaCO_3$. CL 1565-44D contains an alkaline granulation of the same composition.

Sample CL 1565-44A contains 5 gr. of 40 mesh aspirin and CL 1565-44B contains 5 gr. of 12/50 aspirin.

The formula for CL 1565-44D is as follows:

| CL 1565-44D | |
|---|---|
| | wt/gm/capsule |
| Aspirin 10% starch granulation | 0.3611 |
| Alkaline granulation CL 1565-42 | 0.1705 |
| Sta-Rx 1500 | 0.1309 |
| Silicone Fluid 360 | 0.0050 |
| | 0.6675 gm |

The stability of the respective products is measured by the total salicylic acid present in the tablet after storage. The results of this test are summarized in the Table I below.

TABLE I

| | | Total Salicyclic Acid (mg/cap) |
|---|---|---|
| | Initial | 88 Hrs. @ 60° C./60% RH |
| CL 1565-44A | 0.3 | 1.2 |
| CL 1565-44B | 0.2 | 1.1 |
| CL 1565-44D | 0.7 | —* |

*the sample was completely deteriorated

SUMMARY

1. The sample with alkaline granulation was completely deteriorated.

2. The results indicate no significant difference between the capsules with 40 mesh aspirin and aspirin 10% starch granulation Although the invention has been described with reference to specific forms thereof, it will be understood that many changes and modifications may be made without departing from the spirit of this invention:

What is claimed is:

1. As a unit dosage form a capsule having incorporated therein an alkaline tablet having a fast distintegration rate and an aspirin mixture; said aspirin mixture being present in said capsule as a powder or granulated material; said aspirin being present in said capsule at a level in the range of from about 160 mg. to about 500 mg. per capsule; and the quantity of alkaline material contained in said capsule being between about 30% to about 100% by weight based on the total weight of aspirin contained in the capsule.

2. A unit dosage form according to claim 1 in which said alkaline tablet has a thickness in the range of from about 0.210″ to 0.225″.

3. A unit dosage form according to claim 2 in which said tablet has the form of a spheroid or near spheroid.

4. A unit dosage form according to claim 2 in which the aspirin is present in said capsule at a level in the range of from about 400 mg. to about 500 mg. per capsule.

5. A unit dosage form according to claim 4 wherein the alkaline material contained in said capsule is between about 30% to about 100% by weight based on the total weight of the aspirin contained in the capsule.

6. A unit dosage form according to claims 1, 2, 3, 4 or 5 in which the alkaline tablet comprises a mixture of alkaline materials.

7. A unit dosage form according to claim 6 in which said mixture of alkaline materials comprises magnesium carbonate and calcium carbonate.

8. A unit dosage form according to claim 7 in which the ratio of calcium carbonate to magnesium carbonate on a weight basis present in said capsule is within the range of from 1:1 to 3:1.

9. A unit dosage form according to claim 1 in which at least one additional pharmaceutically active ingredient is contained in said capsule.

10. A unit dosage form according to claim 9 in which said additional pharmaceutically active ingredient is an additional analgesic.

11. A unit dosage form according to claim 9 in which said additional pharmaceutically active ingredient is a decongestant.

12. A unit dosage form according to claim 9 in which said additional pharmaceutically active ingredient is an antihistamine.

13. A unit dosage form according to claim 9 in which said additional active ingredients is a mixture of decongestant, antihistamine and antitussive.

* * * * *

UNITED STATES PATENT AND TRADEMARK OFFICE
CERTIFICATE OF CORRECTION

PATENT NO. : 4,294,819

DATED : October 13, 1981

INVENTOR(S) : Thomas M. Tencza

It is certified that error appears in the above-identified patent and that said Letters Patent are hereby corrected as shown below:

Column 5, Example 1, line 48, change

"carbonate" to read -- Magnesium carbonate --

Signed and Sealed this

Eighth Day of December 1981

[SEAL]

Attest:

GERALD J. MOSSINGHOFF

Attesting Officer    Commissioner of Patents and Trademarks